(12) United States Patent
Beumer et al.

(10) Patent No.: US 10,752,569 B2
(45) Date of Patent: Aug. 25, 2020

(54) PROCESS FOR THE MANUFACTURE OF 2,6-DIMETHYL-5-HEPTEN-1-AL

(71) Applicant: DSM IP ASSETS B.V., Heerlen (NL)

(72) Inventors: Raphael Beumer, Kaiseraugst (CH); Werner Bonrath, Kaiseraugst (CH); Frank Eisele, Kaiseraugst (CH); Jocelyn Fischesser, Kaiseraugst (CH); Christof Wehrli, Kaiseraugst (CH)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 16/340,197

(22) PCT Filed: Oct. 12, 2017

(86) PCT No.: PCT/EP2017/076087
§ 371 (c)(1),
(2) Date: Apr. 8, 2019

(87) PCT Pub. No.: WO2018/069456
PCT Pub. Date: Apr. 19, 2018

(65) Prior Publication Data
US 2019/0308923 A1    Oct. 10, 2019

(30) Foreign Application Priority Data

Oct. 12, 2016  (EP) ..................................... 16193513

(51) Int. Cl.
*C07C 45/78*   (2006.01)
*C07C 45/58*   (2006.01)
*C07D 301/02*  (2006.01)

(52) U.S. Cl.
CPC ............ *C07C 45/58* (2013.01); *C07D 301/02* (2013.01)

(58) Field of Classification Search
CPC ..................................................... C07C 45/48
See application file for complete search history.

(56) References Cited

U.S. PATENT DOCUMENTS 4,242,281 A    12/1980  Sprecker et al.

OTHER PUBLICATIONS

International Search Report for PCT/EP2017/076087, dated Feb. 5, 2018, 3 pages.
Written Opinion of the ISA for PCT/EP2017/076087, dated Feb. 5, 2018, 5 pages.
Ni, Wei-zhong et al., "Preparation of 2,6-Dimethyl-5-Heptenal by Reactive Distillation", Shandong Huagong=Shandong Chemical Industry, vol. 40, No. 6, Jan. 1, 2011, pp. 31-32.

*Primary Examiner* — Sikarl A Witherspoon
(74) *Attorney, Agent, or Firm* — Nixon & Vanderhye P.C.

(57) ABSTRACT

The present invention relates to an improved process for the manufacture of 2,6-dimethyl-5-hepten-1-al.

8 Claims, No Drawings

PROCESS FOR THE MANUFACTURE OF 2,6-DIMETHYL-5-HEPTEN-1-AL

This application is the U.S. national phase of International Application No. PCT/EP2017/076087 filed 12 Oct. 2017, which designated the U.S. and claims priority to EP Patent Application No. 16193513.5 filed 12 Oct. 2016, the entire contents of each of which are hereby incorporated by reference.

The present invention relates to an improved process for the manufacture of 2,6-dimethyl-5-hepten-1-al.

2,6-Dimethyl-5-hepten-1-al (compound of formula (I))

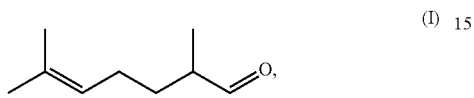

which is also known under the tradename Melonal® was identified first in ginger. 2,6-Dimethyl-5-hepten-1-al is a liquid with a yellow colour. The odor of this compound is described mainly as green, cucumber and melon-like.

2,6-Dimethyl-5-hepten-1-al is used in many fragrance applications and it is very important to create melon and cucumber notes.

2,6-Dimethyl-5-hepten-1-al can be prepared from 6-methyl-5-hepten-2-one by Darzens reaction followed by saponification and decarboxylation.

It is known from U.S. Pat. No. 4,242,281 to synthesize 2,6-dimethyl-5-hepten-1-al according to the following scheme:

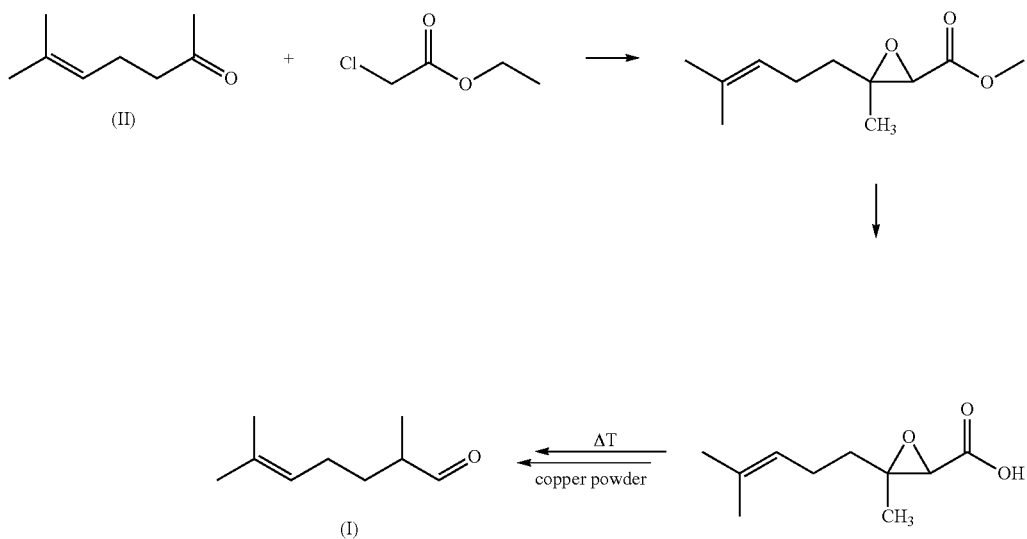

The product, however, still comprises a significant amount of the starting material (6-methyl-5-hepten-2-one, which is the compound of formula (II)).

A lot of time and effort are needed to remove 6-methyl-5-hepten-2-one from the final product. This adds disadvantageously to the overall costs of the process. As 6-methyl-5-hepten-2-one has its own intensive odor profile it may suppress the odor from Melonal® itself.

Furthermore, the decarboxylation (in the process known from the prior art) is done by two consecutive distillations wherein also copper powder is needed. Due to the copper a lot of waste is produced. The disposal of this waste is expensive and leads to an overall increase of the production cost.

Therefore, the objective of the invention was to find an improved process for the manufacture of 2,6-dimethyl-5-hepten-1-al, which does not have the disadvantages as mentioned above.

It was found that the following improved synthesis of 2,6-dimethyl-5-hepten-1-al allows to produce it with a better conversion (less starting material in the final product).

The synthesis of 2,6-dimethyl-5-hepten-1-al is carried out according to the following reaction scheme:

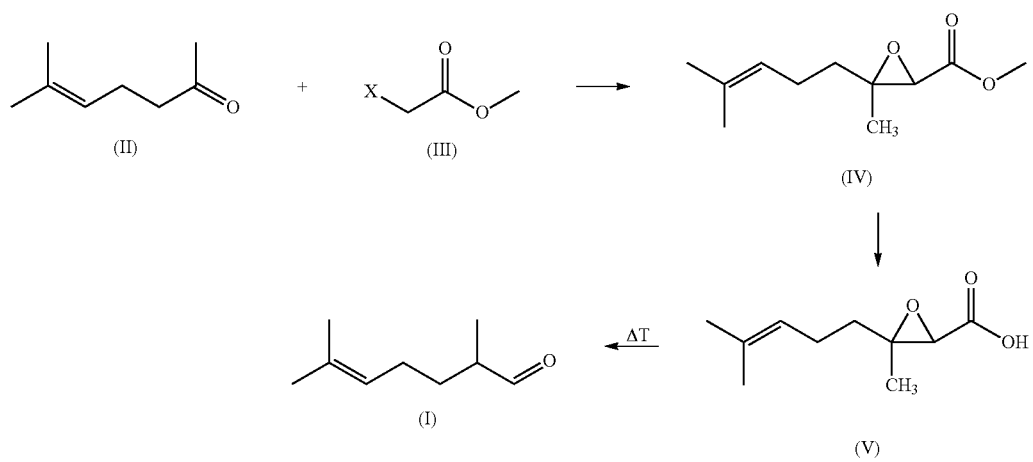

It was found that it is very advantageous to use NaOR with R being $C_{1-4}$-alkyl (preferably R is methyl or ethyl; more preferably R is methyl) as a base and methyl chloroacetate or methyl bromoacetate as α-haloester at a low temperature, preferably at a temperature ≤−15° C., in the first step (reaction of compound (II) and (III) to compound (IV)).

Furthermore, the decarboxylation can be carried out also in a continuous manner; additionally, the decarboxylation is carried out without any metal powder.

Therefore, the present invention relates to a process (P) for the manufacture of the compound of formula (I)

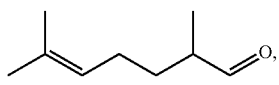
(I)

wherein in a first step i) a Darzens reaction is carried out with a compound of formula (II)

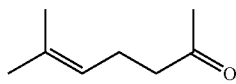
(II)

and a compound of formula (III)

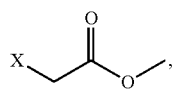
(III)

wherein X is Cl or Br, preferably Cl,
in the presence of NaOR with R being $C_{1-4}$-alkyl (preferably in the presence of $NaOCH_3$) (step (ia))
followed by a saponification reaction (step (ib)) to form the compound of formula (V)

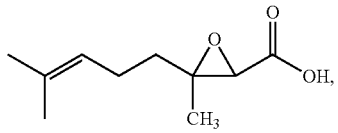
(V)

and wherein in a second step ii) the compound of formula (V) is undergoing a decarboxylation reaction to form the compound of formula (I).

In the following the process steps are discussed in more detail.

Step (i)

Step i) is in fact two steps (step (ia) and step (ib)) which are done in sequence without isolating the reaction product of the first reaction step (compound of formula (IV)).

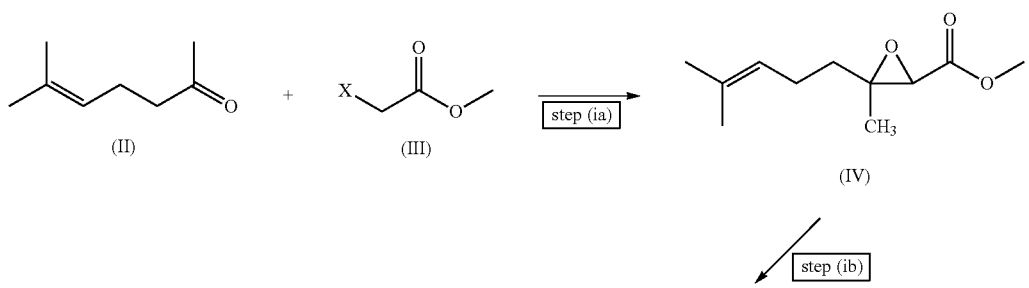

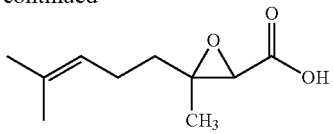

(V)

Step (ia) is a glycidic ester condensation, whereby an α,β-epoxy ester (=glycidic ester) is formed, which is then (step (ib)) saponified into the corresponding acid.

It was found that it is very advantageous to use NaOR with R being $C_{1-4}$-alkyl, preferably to use $NaOCH_3$, as a base and methyl chloroacetate or methyl bromoaceate (preferably methyl chloroacetate) as α-haloester at a low temperature, preferably at a temperature ≤−15° C.

After the glycidic ester condensation took place, remaining base can be neutralized with an acid.

Step iib) is the saponification of the glycidic ester (the α,β-epoxy ester of formula (IV)) into the corresponding acid (compound of formula (V)). It is preferably carried out in the presence of a strong base. Example of such a base is NaOH. Excess of the base is neutralized after the reaction with an acid such as HCl or $H_2SO_4$.

Due to these reaction conditions the conversion of the starting material is increased significantly.

The reaction of step (i) (step (ia) and step (ib)) is usually carried out in a solvent (or a mixture of solvents). Suitable solvents are aliphatic hydrocarbons or aromatic hydrocarbons. Examples of aliphatic hydrocarbons are straight and branched $C_{6-10}$-alkanes and $C_{6-10}$-cylcoalkanes such as cyclohexane, n-hexane and n-heptane. Examples of aromatic hydrocarbons are benzene, toluene, o-xylene, m-xylene and p-xylene. Especially suitable are cyclohexane, n-hexane, n-heptane, benzene, o-xylene, m-xylene, p-xylene or toluene. Preferred are n-hexane, n-heptane and toluene. Most preferred is toluene.

Therefore, the present invention relates to a process (P1), which is process (P), wherein step (i) is carried out in at least one solvent.

Therefore, the present invention relates to a process (P1'), which is process (P1), wherein step (i) is carried out in at least one aliphatic hydrocarbon or at least one aromatic hydrocarbon.

Therefore, the present invention relates to a process (P1"), which is process (P1), wherein step (i) is carried out in at least one solvent chosen from the group consisting of n-hexane, n-heptane, benzene, o-xylene, m-xylene, p-xylene and toluene.

The reaction temperature of step (ia) is ≤−15° C. Preferably the reaction temperature is in a range of from −45° C. to −15° C. More preferably the reaction temperature is in a range of from −30° C. to −15° C.

Therefore, the present invention relates to a process (P2), which is process (P), (P1), (P1') or (P1"), wherein step (ia) is carried out at a reaction temperature of ≤−15° C.

Therefore, the present invention relates to a process (P2'), which is process (P), (P1), (P1') or (P1"), wherein step (ia) is carried out at a reaction temperature in the range of from −45° C. to −15° C.

Therefore, the present invention relates to a process (P2"), which is process (P), (P1), (P1') or (P1"), wherein step (ia) is carried out at a reaction temperature in the range of from −30° C. to −15° C.

The starting materials, compound (II) and compound (III), can be added in equimolar amounts with respect to each other. Preferably compound of formula (III) is added in excess, i.e. the molar ratio of the compound of the formula (III) to the compound of formula (II) is in the range of from 1.1:1 to 2:1.

Step (ib) is usually carried out at slightly elevated temperature; preferably up to 60° C.

Therefore, the present invention relates to a process (P3), which is process (P), (P1), (P1'), (P1"), (P2), (P2') or (P2"), wherein step (ib) is carried out at elevated temperature.

Therefore, the present invention relates to a process (P3'), which is process (P), (P1), (P1'), (P1"), (P2), (P2') or (P2"), wherein step (ib) is carried out at a reaction temperature in the range of from 30° C. to 60° C.

The reaction product of step (i), which is the compound of formula (V) is extracted from the reaction mixture by an aliphatic hydrocarbon or by an aromatic hydrocarbon (such as the ones cited above) and it can be washed with an aqueous phase.

Usually the reaction product is not isolated completely but left solved in the solvent (the aliphatic hydrocarbon or the aromatic hydrocarbon).

Step (ii)

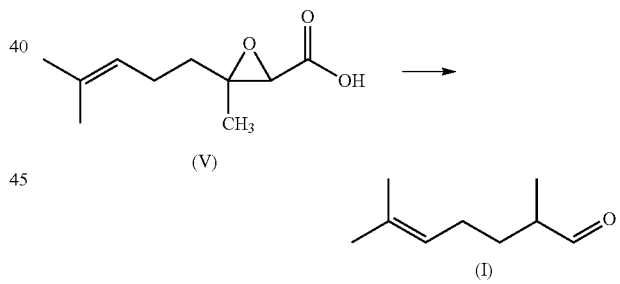

Step (ii) is a decarboxylation step. The reaction product of step (i), which is the compound of formula (V) in at least one aliphatic hydrocarbon or at least one aromatic hydrocarbon, is heated up, preferably to a temperature of ≥160° C., preferably to a temperature in the range of from 160 to 300° C.

After the decarboxylation, the side products are removed by distillation.

These reaction conditions are very mild and no metal powder is needed. In the prior art copper powder is essential for this step. Because the process of the present invention does not need any heavy metals such as copper, it is an ecological process.

The invention is illustrated by the following Example. All percentages are related to the weight and the temperature is given in ° C.

EXAMPLE

In a 500 ml four neck reaction flask with thermometer, Teflon blade stirrer and a 25 ml funnel for solids is provided under nitrogen: 25.24 g of 6-methyl-5-hepten-2-one (200 mmol), 28.22 g of methyl chloroacetate (260 mmol) and 20 ml of toluene. 14.05 g of sodium methylate (260 mmol) is added to the solution in 1 hour at −20° C. and under stirring with 200 rpm (rotations per minute).

The viscous mixture is stirred for 30 minutes at 0° C., followed by addition of 142.5 ml of sodium hydroxide (2 mol/l; 285 mmol). The biphasic mixture is stirred at 300 rpm for 30 minutes at 40° C. (the viscous phase dissolves in about 5 minutes), followed by addition of 50 ml of toluene. The pH is adjusted at 18° C. to pH=2.0 (pH electrode) by adding about 150 ml of sulfuric acid (1 mol/l; 150 mmol).

The glycidic acid is extracted in 2 funnels with 2×30 ml of toluene.

The organic phases are washed in series with 2×20 ml of 5% sodium chloride solution. The organic phases are combined and partially evaporated at the rotavapor (45° C., 50 mbar), police-filtered and concentrated to 70 g at 45° C., 50 mbar to obtain 70 g of glycidic acid (about 44% in toluene).

The solution of the product obtained from (step (i)) is dropped in 90 minutes into a hot reaction flask at 185°-190° C. (bath=215° C.) at a vacuum of 100 mbar, and flushed with 5 ml of toluene in 10 minutes.

The compound of formula (I) is obtained in a yield of 58%.

The invention claimed is:

1. A process for the manufacture of the compound of formula (I):

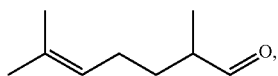

(I)

wherein the process comprises the steps of:
(i) conducting a step (ia) by carrying out a Darzens reaction with a compound of formula (II):

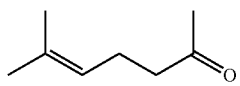

(II)

and a compound of formula (III):

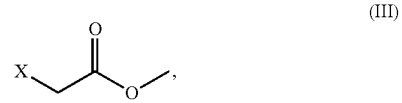

(III)

wherein X is Cl or Br, in the presence of NaOR, wherein R is a $C_{1-4}$-alkyl, and in the presence of at least one hydrocarbon solvent selected from the group consisting of cyclohexane, n-hexane, n-heptane, benzene, o-xylene, m-xylene, p-xylene and toluene, followed by conducting a step (ib) by carrying out a saponification reaction to form the compound of formula (V):

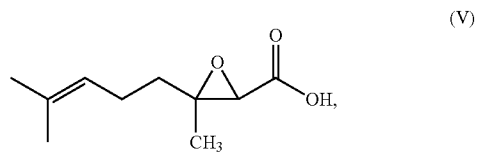

(V)

and thereafter
(ii) subjecting the compound of formula (V) to a decarboxylation reaction to form the compound of formula (I).

2. The process according to claim 1, wherein the reaction temperature of step (ia) is −15° C.

3. The process according to claim 1, wherein step (ib) is carried out at a reaction temperature in the range of from 30° C. to 60° C.

4. The process according to claim 1, wherein step (ii) is carried out at a reaction temperature of at least 160° C.

5. The process according to claim 1, wherein step (ii) is carried out in the absence of a metal powder.

6. The process according to claim 5, wherein step (ii) is carried out in the absence of a copper powder.

7. The process according to claim 2, wherein the reaction temperature of step (ia) is in the range of from −45° C. to −15° C.

8. The process according to claim 2, wherein the reaction temperature of step (ia) is in the range of from −30° C. to −15° C.

* * * * *